US008733283B2

(12) United States Patent
Fidgett et al.

(10) Patent No.: US 8,733,283 B2
(45) Date of Patent: May 27, 2014

(54) METHOD FOR REARING PREDATORY MITES

(75) Inventors: Melvyn John Fidgett, Little Clacton (GB); Clive Stewart Alexander Stinson, Little Clacton (GB)

(73) Assignee: Syngenta Bioline Limited (GB)

( * ) Notice: Subject to any disclaimer, the term of this patent is extended or adjusted under 35 U.S.C. 154(b) by 541 days.

(21) Appl. No.: 12/375,863

(22) PCT Filed: Jul. 26, 2007

(86) PCT No.: PCT/GB2007/002858
§ 371 (c)(1),
(2), (4) Date: Sep. 10, 2009

(87) PCT Pub. No.: WO2008/015393
PCT Pub. Date: Feb. 7, 2008

(65) Prior Publication Data

US 2010/0119645 A1 May 13, 2010

(30) Foreign Application Priority Data

Aug. 2, 2006 (GB) .................................. 0615358.9

(51) Int. Cl.
*A01K 29/00* (2006.01)
*A01K 67/00* (2006.01)
*A23K 1/18* (2006.01)
*A23G 3/00* (2006.01)

(52) U.S. Cl.
USPC ..................... 119/6.5; 800/9; 426/2; 426/658

(58) Field of Classification Search
USPC .................................... 426/2; 119/6.5; 800/9
See application file for complete search history.

(56) References Cited

U.S. PATENT DOCUMENTS

2005/0178337 A1* 8/2005 Wright .......................... 119/6.5

FOREIGN PATENT DOCUMENTS

| GB | 2393890 A | 4/2004 |
|---|---|---|
| WO | 9959402 A | 11/1999 |
| WO | 2006057552 A | 6/2006 |

OTHER PUBLICATIONS

NPL "Wheat Bran" Sun, X et al. entitled "The effects of Wheat Bran Composition on the production . . . Penicillium decumbens" Appl Biochem Biotechnol. 146: 119-128, 2008.*

NPL "Potato Dextrose" in "World Crop Pests" "Eriophyoid Mites, their Biology, natural enemies and control" edited by W. Helle ( Editor-In-Chief) , E.E. Lindquist et al. vol. 6, p. 379, 1996. ISBN : 0-44-88628-1.*

NPL "*Thyreophagus entomophagus*" by Singh A et al. in Mites associated with poultry feed Hisar, Haryana (India). J Entomological Research. 26(3): 2002 (Abstrct).*

NPL "Simple sugar rich media" by Aygun, O et al. in "A survey on . . . dairy product" in J Food Engineering 78: 878-881, 2007 (Available online Jan. 19, 2006).*

NPL mites: http://www.entomology.ucr.edu/ebeling/ebeling7.html [ year 1996; 2002 copyright ; year on last p. 60].*

Zhang, Y et al: Potential of *Amblyseius* cucumeris (*Acari*: phytoseiidae) as a biocontrol agent against schizotetranychus nanjingensis in Fujian, China: Systematic and Applied Acarology Special Publications, Systematic and Applied Acarology Society, London, GB, vol. 4, 2000, pp. 109-124.

Zdarkova, E: "Mites as pests of stored products. 14.1. Application of the bio-preparation 'cheyletin' in empty stores" Modern Agcarology, Academica Prague and SPB Academic Publishing, The Hague, NL, vol. 1, 1991, pp. 607-610.

Ramakers, P J M et al: "Start of commercial production and introduction of *Amblyseius* mckenziei sch. & pr. cacarina" Mededelingen Van De Faculteit Landbouwwetenschappen Universiteit Gent, Gent, BE.

Abou-Awad, B A et al: "Effects of artificial and natural diets on the development and reproduction of two phytoseiid mites *Amblyseius* gossipi and *Amblyseius swirskii* (*Acari*: phytoseiidae)" Insect Science and Its Application, ICIPE Science Press, Nairobi, KE, vol. 13, No. 3, 1992, pp. 441-445.

* cited by examiner

*Primary Examiner* — Humera Sheikh
*Assistant Examiner* — Bhaskar Mukhopadhyay
(74) *Attorney, Agent, or Firm* — Brian D. McAlhaney

(57) ABSTRACT

The present invention relates to the field of biological control. Specifically, it relates to the use of predator mites as biological control agents for reducing damage to crops by insect pests. In particular, it relates to a new method for rearing predator mites, and a method for controlling pests in a crop using predator mites reared using said method.

14 Claims, No Drawings

METHOD FOR REARING PREDATORY MITES

This application is a 371 of International Application No. PCT/GB2007/002858 filed Jul. 26, 2007, which claims priority to GB Application No. 0615358.9 filed Aug. 2, 2006, the contents of which are incorporated herein by reference.

The present invention relates to the field of biological control. Specifically, it relates to the use of predator mites as biological control agents for reducing damage to crops by insect pests. In particular, it relates to a new method for rearing predator mites, and a method for controlling pests in a crop using predator mites reared using said method.

Plant pests are a major factor in the loss of the world's important agricultural crops. About $8 billion is lost every year in the U.S. due to infestations of plants by non-mammalian pests including insects. In addition to losses in field crops, insect pests are also a burden to vegetable and fruit growers, to producers of ornamental flowers, and to home gardeners. For example, pest thrips such as *Frankliniella occidentalis*, and whitefly such as *Bemisia tabaci* cause extensive damage to horticultural crops such as salad vegetables, cut flowers and ornamental plants, resulting in significant economic loss to the growers.

Insect pests are mainly controlled by intensive applications of chemical pesticides, which are active through inhibition of insect growth, prevention of insect feeding or reproduction, or cause death. Although the use of such chemicals can result in good control of insect pests, the widespread use of chemical pesticides can result in the appearance of resistant insect varieties. Further, high levels of chemicals on horticultural crops, in particular salad vegetables, are undesirable to many consumers.

Therefore, an alternative method of pest control involving the use of beneficial insects or mites has been developed. The beneficial insects or mites are predatory towards pest insects such as thrips, and can be applied to crops to control insect pests. Beneficial insects or mites can be provided to crop plants in a variety of ways, for example manually or through a controlled release device. The use of beneficial insects or mites forms part of integrated crop management and integrated pest management programs, combining cultural, biological and chemical means to achieve sustainable pest control.

One example of a beneficial insect or mite system is the use of *Amblyseius cucumeris* as a predatory mite for the control of pest thrips. Existing systems involve the mite being provided either loose in bran and vermiculite for sprinkling onto crops, or in sachets for longer periods of protection. *Amblyseius cucumeris* feed on first instar thrips larvae, and control relies on complete cover of a crop with the predator before thrips establish. Recently, *Amblyseius swirskii* has been introduced as an alternative predatory mite to *Amblyseius cucumeris*. It is rapidly becoming the predatory mite of choice amongst growers because it can be used for the control of both thrips and whitefly.

Mass rearing systems that were suitable for generating large numbers of beneficial insects and mites were first introduced approximately 70 years ago. Original mass rearing systems were based on the provision of a natural food source of the insect or mite to be reared. For example, mass rearing systems can be based on the provision of host species such as *Tetranychus urticae* for *Amblyseius swirskii* or *Phytoseiulus persimilis*, pollen grains for other predatory mites, or aphids for *Aphidoletes aphidimyza*. More recently, mass rearing systems for predatory mites have been successfully developed using factitious hosts. The most commonly used hosts are stored product mites such as *Tyrophagus putrescentiae*, *Acarus siro*, and *Carpoglyphus lactis*. Through the provision of predator mites, prey mites, and a food source for the prey mites, a stable breeding colony can be established to allow the rearing of a continuous supply of predator mites.

GB2393890 discloses that *A. cucumeris* can be reared using *Tyrophagus putrescentiae*, *T. tropicus*, or *Acarus siro*. Ramakers et al. (Bulletin-SROP 6(3), 203-206) discloses that rearing of *Amblyseius mckenziei* and *A. cucumeris* can be carried out using wheat bran as the primary food source and *Acarus farris* as substitute prey. Nomikou et al. (Experimental and Applied Acarology 27 (1-2), 57-68) discloses that *Tyrophagus putrescentiae* can be used as a food source for *Typhlodromips* (*Amblyseius*) *swirskii*, for obtaining high predator/prey ratios. Steiner et al. (Australian Journal of Entomology 42, 124-130) discloses that *Tyrophagus putrescentiae* can be used as a food source for *Typhlodromips montdorensis*. WO2006/057552 discloses that *Amblyseius swirskii* can be reared on Astigmatid mites, such as mites from the families Carpoglyphidae, Pyroglyphidae, Glyciphagidae or Acaridae. In particular, it discloses that *Carpoglyphus lactis* can be used as a prey mite for rearing *A. swirskii*. CN1440646 describes the use of various species of stored product mite for raising the predatory mite, *Amblyseius cucumeris*.

One disadvantage to the existing mass rearing systems is that the speed of growth of the predator colony is limited. Therefore, there exists a need for an improved mass rearing system that will result in a faster breeding rate of the predator colony. The present invention overcomes this problem through the provision of a better food source. In conventional mass rearing systems, predator mites tend to feed mainly on the eggs of prey mite. One reason for this is that the juvenile and adult forms of most grain mites that are used as prey are quite hairy. The present invention relates to the use of a prey mite that is less hairy than most other Astigmatid mites, and therefore predators feed well on adults and juveniles as well as eggs.

Another problem associated with existing mass rearing systems is that breeding populations of predator mites are very sensitive, and can be easily affected by changes in environmental conditions. Many mites that are conventionally used as prey mites are very mobile. Their rapid and continuous movement disturbs predator mites, which in turn causes stress, and upsets reproduction, egg laying and feeding. In turn, the quality and number of predator mites reared decreases. The present invention solves this problem through use of a less active mite as the prey mite, which causes less disturbance to predator colonies, in turn resulting in a greater number of healthier predator mites being produced. Another problem with many mites that are conventionally used as prey mites is that they can generate high levels of metabolic heat and carbon dioxide, which can also have a detrimental effect on the health and size of the predator colony. The present invention solves this problem through use of less active mites that generate less metabolic heat and carbon dioxide.

According to the present invention there is provided a method for rearing predatory mites, comprising providing *Thyreophagus entomophagus* as prey mites, and allowing the predatory mites to feed on said prey mites.

In the present context, the term "rearing" refers broadly to breeding, reproducing, surviving and growing of predatory mites. Rearing can be in an open or closed environment. Typically it will take place in a closed environment, such as a growth room or incubator.

The growth of a predator colony may be assessed by monitoring the time between generation periods, the rate of egg production (oviposition rates), and/or fecundity.

The term "prey mites" refers to mites that are present specifically as prey for the predatory mites to feed on. The predatory mites may feed on any life stage of the prey mite, for example eggs, juveniles or adults.

The term "predatory mites" refers to mites that are predators of any pest. In particular, it refers to mites that are predators of crop pests. They may be predators of pests such as insects, nematodes or arachnids. Typically, the predator mites will be useful for control of common crop pests such as thrips and whitefly. Most predatory mites belong to the family Phytoseiidae (order Acarina). The most common predatory mites used for biological control in glasshouses are *Amblyseius swirskii, Phytoseiulus persimilis, Amblyseius californicus, Amblyseius cucumeris, Amblyseius degenerans* and *Hypoaspis miles.*

*Amblyseius* (*Typhlodromips*) *swirskii* is used principally for the control of thrips, such as *Frankliniella occidentalis* or *Thrips tabaci*, and whitefly, such as *Trialeurodes vaporariorum* or *Bemisia tabaci*. It is found in eastern Mediterranean regions including Israel, Italy, Cyprus and Egypt. It is well suited to a warm and humid climate.

*Phytoseiulus persimilis* is used in biological control programs for two-spotted spider mites (*Tetranychus urticae*), and related *Tetranychus* species. The mites are predators as nymphs and adults, mostly feeding on spider mite eggs and nymphs, but also consuming adults. Since *P. persimilis* is an obligate spider mite predator and cannot survive on alternate food sources such as pollen, survival tends to be poor if prey is in short supply.

*Amblyseius* (*Neoseiulus*) *californicus* is an active predatory mite that has specialised in feeding on mites in the family Tetranychidae. This includes the common Red Spider Mite or Two-Spot Mite *Tetranychus urticae*, and the Carmine Mite *Tetranychus cinnabarinus*. It is less specialised than *Phytoseiulus persimilis*, and while it prefers to feed on spider mites, it can feed and reproduce on other arthropod prey or pollen. Where few spider mites are present, it is able to survive by feeding on these alternative sources of food, and so can persist in a crop longer than *Phytoseiulus persimilis.*

*Amblyseius* (*Neoseiulus*) cucumeris is used to control thrips, including the Western Flower Thrips (*Frankliniella occidentalis*). The main food source is first-instar thrips larvae. Later stage larvae and adults are less susceptible due to the small size of the mite. Since *A. cucumeris* can also feed on other mites (such as cyclamen mites and broad mites) as well as pollen, it can survive in many different situations.

*Amblyseius* (*Iphiseius*) degenerans, is more aggressive than *A. cucumeris* in attacking thrips, and usually colonises flowers in greater numbers. *A. degenerans* will also feed on spider mites and pollen.

*Hypoaspis miles* mites, from the family Laelapidae, live in soil and other growing media. They feed on fungus gnat larvae, springtails and also thrips pre-pupae and pupae. With the range of food eaten by these predators, they can become established and persist for long periods. Since this predator lives under the surface of the growing media, it can escape contact with many pesticides that are used to control pests that feed on leaves and flowers.

Other predatory mites include *Euseius tularensis, Typhlodronzus occidentalis, Typhlodromus pyri, Zetzellia mali, Amblyseius* (*Iphiseius*) *degenerans, Amblyseius* (*Kanzpinzodromus*) *aberrans, Amblyseius* (*Neoseiulus*) *barkeri, Amblyseius andersoni, Amblyseius* (*Neoseiulus*) *fallacis, Amblyseius* (*Euseius*) *finlandicus, Amblyseius* (*Typhlodromalus*) *lailae, Amblyseius* (*Typhlodronzalus*) *limonicus, Amblyseius* (*Typhlodromips*) *montdorensis, Amblyseius* (*Euseius*) *ovalis, Amblyseius* (*Euseius*) *scutalis, Amblyseius* (*Euseius*) *stipulatus* and *Amblyseius* (*Neoseiulus*) *womersleyi* (also known as *Amblyseius longispinosus*). This list is not exhaustive. McMurtry et al. (Annual Review of Entomology 42, 291-321) categorises the diversity of life-stages in the Phytoseiidae based mainly on food habitats and related biological and morphological traits. As mite taxonomy is continually changing, the number and species of mites classified as predatory mites may change (see for example the Catalogue of Phytoseiidae by Moraes et al. published in 2004 that lists 2,250 species, compared to the previous edition published in 1986 that listed only 1500 species).

The present invention relates to the use of *Thyreophagus entomophagus* as a food source for any predatory mite. In particular, the predatory mites may be selected from the group consisting of *Amblyseius* (*Typhlodromips*) *swirskii, Phytoseiulus persimilis, Amblyseius cucumeris, Amblyseius degenerans, Hypoaspis miles, Euseius tularensis, Typhlodromus occidentalis, Typhlodromus gyri, Amblysieus fallacies, Zetzellia mali, Amblyseius* (*Iphiseius*) *degenerans, Amblyseius* (*Kampimodromus*) *aberrans, Amblyseius* (*Neoseiulus*) *barkeri, Amblyseius andersoni, Amblyseius* (*Neoseiulus*) *fallacis, Amblyseius* (*Euseius*) *finlandicus, Amblyseius* (*Typhlodromalus*) *lailae, Amblyseius* (*Typhiodromalus*) *limonicus, Amblyseius* (*Typhlodromips*) *montdorensis, Amblyseius* (*Euseius*) *ovalis, Amblyseius* (*Euseius*) *scutalis, Amblyseius* (*Euseius*) *stipulatus* and *Amblyseius* (*Neoseiulus*) *womersleyi* (also known as *Amblyseius longispinosus*).

The prey mite *Thyreophagus entomophagus* (Laboulbene, 1852) is also known as *Acarus entomophagus, Histiogaster entomophagus, Histiogaster aleurophagus, Tyroglyphus malus*, and *Dermaleichus malus.*

The body of the *Thyreophagus entomophagus* male is elongated and oval, with a colourless shining cuticle and pale brown stumpy legs. At its posterior end, the hysterosoma is extended backwards as a horizontal semicircular shelf in the same plane as the ventral surface of the body, and with a well-sclerotized ventral surface. The propodsomal dorsal shield extends as far back as the scapular setae, but the rest of the surface of the idiosoma has a naked appearance because of the scarcity of setae. The body of the *Thyreophagus entomophagus* female is longer and more slender than that of the male, the posterior end being slightly pointed and not prolonged into an opisthiosomal lobe. The genital opening lies between coxae iii and IGV, and is well separated from the anus, which extends as far back as the posterior edge of the body; two pairs of long anal setae arise on either side of it. The chaetoatxy of body and legs is the same as that of the male, except that a small spine is present at the base of all the claws.

*Thyreophagus entomophagus* is a largely sedentary mite which shows no inclination to move away from suitable food supplies, even when disturbed. It does not avoid predators, and has no visible defence mechanisms against them. Predators can be seen recoiling from adults of *Tyrophagus putrescentiae*, suggesting the existence of an active, possibly chemically-based, defence mechanism.

Usually, predator mites feed on the egg stages of mite hosts. One reason for this is that the juvenile and adult stages of the many mite hosts such as *Carpoglyphus lactis* and *Tyrophagus putrescentiae* are quite hairy. This makes the prey mites less attractive to predators. However, since the adult form of *Thyreophagus entomophagus* is less hairy, predator mites readily feed on the juveniles and adults, as well as eggs. Therefore, *Thyreophagus entomophagus* is a better prey because predator mites can attack more stages of the mite life cycle.

Further, *Thyreophagus entoniophagus* is a fairly sessile mite. It is less active and slower moving than other mites that have previously been used as prey, such as *Carpoglyphus lactis, Acarus siro* and *Tyrophagus putrescentiae*. Breeding cultures of mites are very sensitive, and can be easily disrupted. In breeding cultures, predators are easily disturbed by very active or mobile prey mites. It is important to minimise disruption to the predator mites, because disturbance will result in decreased egg-laying. Also, disturbing the juvenile predators will upset their feeding and cause stress, in turn reducing their chances of developing into healthy adult predators. With mobile prey species, as the ratio of prey to predator increases (for example due to reduced egg laying, or reduced numbers of juveniles developing into adults) there will be a further negative effect on the reproduction of the predator mites due to a greater level of disturbance in the rearing medium. Another effect of the ratio of prey to predator increasing is that there is an increase in metabolic heat, frass and fungal organisms within the breeding culture. This will again have a detrimental effect on the reproduction and quality of the predators in the culture.

Mites such as *Carpoglyphus lactis* and *Tyrophagus putrescentiae* that are conventionally used as prey for rearing predatory mites, produce alarm pheromones when attacked, or when present in high numbers. This contributes to their activity, and further increases the level of disturbance in the rearing medium. No similar pheromone is reported for *Thyreophagus entomophagus*.

In one aspect of the present invention, the prey mites will be present as a breeding population. In this way, there will be an adequate food source for the predatory mites that is continuously replenished. Predatory mites may feed on one or more of the life cycle stages of the prey mite including eggs, larval stages, nymphs, juveniles and/or adults.

In one aspect of the present invention, the predatory mites are from the family Phytoseiidae. The taxonomy of mites is still evolving. The Zootaxa catalogue (De Moraes, McMurty, Denmark & Campos, 2004, Zootaxa 434, 1-494) describes the current understanding of the taxonomy of the Phytoseiidae, and lists all known members of this family. In another aspect of the invention, the predatory mites are from the subfamily Amblyseiinae. In a further aspect of the invention, the predatory mites are from a genus selected from the group consisting of *Amblyseius, Typhiodromips, Neoseiulus, Typhlodromalus, Euseius, Typhlodromus, Iphiseius* and *Kampimodromus*.

In a further aspect of the invention, the predatory mites are from the genus *Amblyseius*. Examples of predatory mites from this genus include *Amblyseius* (*Kampinodromus*) *aberrans, Amblyseius* (*Neoseiulus*) *barkeri, Amblyseius andersoni, Amblyseius* (*Neoseiulus*) *californicus, Amblyseius* (*Neoseiulus*) *cucumeris, Amblyseius degenerans, Amblyseius* (*Neoseiulus*) *fallacis, Amblyseius* (*Euseius*) *finlandicus, Amblyseius* (*Typhlodromalus*) *lailae, Amblyseius* (*Typhlodromalus*) *limonicus, Amblyseius* (*Typhlodromips*) *montdorensis, Amblyseius* (*Euseius*) *ovalis, Amblyseius* (*Euseius*) *scutalis, Amblyseius* (*Euseius*) *stipulatus, Amblyseius* (*Typhlodromips*) *swirskii*, and *Amblyseius* (*Neoseiulus*) *womersleyi* (also known as *Amblyseius longispinosus*). The predatory mites may, for example, be *Amblyseius andersoni, Amblyseius californicus, Amblyseius cucumeris, Amblyseius fallacis, Amblyseius limonicus, Amblyseius montdorensis, Amblyseius ovalis, Amblyseius stipulatus, Amblyseius swirskii* or *Amblyseius womersleyi*. In a preferred aspect of the invention, the predatory mites are *Amblyseius swirskii*. This mite is also known as *Typhlodromips swirskii*, and these names are used synonymously herein.

The present invention may be used to provide a source of predator mites for the control of pest insects. A particular predator will be selected on the basis of the target pest to be controlled, and the crop to which the predator will be applied.

For example, the predator mites may be used to control one or more of the pests from the following, non-exhaustive list: *Tetranychus* spp. including but not restricted to *Tetranychus urticae, T. cinnabarinus, T. kanzawai, T. turkestani, T. occidentalis; Oligonychus* spp.; *Panonychus ulmi* and *P. citri*; Eriophyid mites including but not restricted to *Aculops lycopersici, Aculus schlectendali, Phyllocoptruta oleivora, Aceria ficus, Rhyncaphytoptus ficifoliae*; Tarsonemid mites including but not restricted to *Polyphagotarsonemus latus, Phytonemus pallidus*; thrips pests including but not restricted to *Frankliniella occidentalis, F. intonsa, F. schultzei, Thrips tabaci, T. palmi, Echinothrips americanus, Heliothrips haemorrhoidalis*; and whitefly pests including but not restricted to *Trialeurodes vaporariorum, Bemisia tabaci, Aleyrodes proletella, A. lonicerae*.

It will be preferable to choose a predator that will not cause damage to the crop plant itself. The predator mites may be used to control pests on one or more of the crop plants in the following, non-exhaustive list: tomato, sweet pepper, chilli pepper, aubergine, cucumber, beans, squash, melon, strawberry, raspberry, banana, papaya, apple, pear, plum, grape, rose, chrysanthemum, Gerbera, Begonia, Cyclamen, Poinsettia, Citrus, Skimmia, Choiysia, Daphne and Magnolia. Suitably, the crop is selected from the group consisting of peppers, cucumbers, aubergines, roses, gerberas, melons and beans, especially when In one embodiment, the present invention may be used to provide a source of predator mites for the control of thrips (such as *Frankliniella occidentalis* or *Thrips tabaci*) and/or whitefly (such as *Trialeurodes vaporariorum* or *Bemisia tabaci*). In particular, the present invention may be used to provide a source of *Amblyseius swirskii* mites for the control of thrips and/or whitefly.

It is important to use an appropriate starting ratio of predator mites to prey mites. For *Amblyseius cucumeris* reared on *Tyrophagus putrescentiae*, predator:prey ratios are normally between 1:4 and 1:10. Higher ratios usually mean that the colony will be overwhelmed by *Tyrophagus*. For *Amblyseius swirskii* reared on *Carpoglyphus lactis*, the ratio is normally between 1:4 and 1:10. In contrast, for predator mites reared on *Thyreophagus entomphagus*, a higher starting ratio of predator:prey is required. The optimum ratio will vary depending on the nature of the predator species being reared. For predators mites reared on *Thyreophagus entomophagus*, the preferred starting predator:prey ratio is between 1:10 and 1:100. Suitably it is between 1:20 and 1:80. More suitably it is between 1:30 and 1:70. In one embodiment, the starting ratio is at least 1:30. In another embodiment, it is between 1:40 and 1:60. In a further embodiment, the starting predator:prey ratio is approximately 1:50. In a further embodiment still, the starting ratio is at least 1:50. Since the cultures of both the predator and prey mites are actively reproducing, the ratio of predator to prey mites may change over time.

For a reliable, consistent mass rearing of *Amblyseius swirskii*, a suitable starting ratio of *Thyreophagus entomophagus: Amblyseius swirskii* is approximately 1:50. Below this the production may be unstable as there is a risk of the *Thyreophagus entomophagus* mites being completely consumed before the breeding cycle has been completed. The consequence of this will be a reduced end yield due to cannibalism and reduced breeding, and less healthy predators due to starving.

For mass-rearing of *Amblyseius andersoni* on *Thyreophagus entomophagus*, all the prey mites will be completely consumed if the predator:prey ratio at the initial set up inoculation is below approximately 1:30. More voracious and/or faster reproducing predator species such as *Amblyseius cucumeris* would require an even higher initial predator:prey ratio in order for the predator:prey balance to be maintained through the entire cycle and so provide the optimum end cycle predator concentration in the production system. The person skilled in the art is familiar with the need to optimise the starting ratio of predator mites to prey mites for each species combination.

*Thyreophagus entomophagus* can be reared on a variety of diets. Suitably, it is reared on a high carbohydrate yeast-based diet. In this context, a diet that contains at least 5% sugar is a high carbohydrate diet. The diet is mixed with bran as a carrier in a ratio of approximately 20% diet:80% bran (v/v). The mites can be reared in the medium in a plastic container, typically ranging in size from 30 ml to 10 liters. The containers are vented with 60 micron nylon mesh discs.

During rearing of *Thyreophagus entomophagus* there are a number of production stages. At each stage, small numbers of *Thyreophagus entomophagus* mites are inoculated into the containers and placed in a room having suitable conditions for allowing the mites to reproduce. Suitably the temperature in the room is in the range from 15°-30° C. and the humidity between 70-95% r.h. Most suitably, the temperature is approximately 28° C. The cycle time from inoculation to end product ranges from 7-21 days. Suitably, it is approximately 14 days. The rate of reproduction in these conditions will be sufficient to produce an end culture concentration of around 2 million mobile stages of *Thyreophagus entomophagus* and eggs from a starting concentration of around 50,000 mites per liter.

According to the present invention, there is provided a composition comprising at least one predatory mite, and *Thyreophagus entomophagus* as a food source for said predatory mite.

In one embodiment, the composition is self-sustaining. It includes a food source for the prey mite, which in turn is a food source for the predator mite. In one aspect of the invention, the composition comprises a population of predatory mites. The population may be a breeding population so that the composition provides a continuous supply of predatory mites. In another aspect of the invention, the *Thyreophagus entomophagus* is a population of prey mites. Again, this population may be a breeding population so that the composition provides a continuous supply of prey mites as food for the predatory mites. In a further aspect of the invention, the composition may comprise other food sources for the predatory mites in addition to the *Thyreophagus entomophagus* prey mites. Other food sources may include natural prey of the predators such as *Tetranychus urticae* for the predator *Amblyseius swirskii*, honeydew, baker's yeast or pollen. The pollen may be from any suitable source, such as the date palm plant *Phoenix dactylifera*, or the castor oil plant *Ricinus communis.*

The composition may be employed as a means for rearing large numbers of predator mites. In one embodiment, the composition is used as a means of rearing large numbers of *Amblyseius swirskii* predator mites. Alternatively, the composition may be packaged in such a way that it can be placed directly in a crop environment. Since the composition is self-sustaining, it can be placed directly into a cropping environment where it can be used to provide a continuous source of predator mites for a prolonged period of time. In one embodiment, the composition will be self-sustaining for at least a week. In another embodiment, the composition will be self-sustaining for a least a month. In a further embodiment, the composition will be self-sustaining for 6 weeks or more. In one aspect of the invention, the ratio of predator to prey mites in the composition will be adjusted to ensure that the rate of supply of predator mites remains approximately constant for a period of at least a week. In one aspect of the invention, the ratio of predator to prey mites in the composition will be adjusted to ensure that the rate of supply of predator mites remains approximately constant for a period of at least a month. In a further aspect of the invention, the ratio of predator to prey mites in the composition will be adjusted to ensure that the rate of supply of predator mites remains approximately constant for a period of 6 weeks or more.

Suitable cropping environments include, but are not limited to, glasshouses, greenhouses, polytunnels, shade houses (for example netting structures used for ornamentals and field grown crops of peppers and tomatoes), orchards, fields (for example for strawberry and raspberry crops) and gardens (for example market gardens and botanical gardens).

The composition may be delivered to the crop via any suitable delivery system, ranging from simple devices such as pots, bottles, boxes, cartons, bags, tubes and sachets to more complex devices such as the Gemini™ twin sachet (as described in GB2393890), blowing devices which carry product onto the crop in a stream of air or liquid, and rotary devices which distribute product mechanically into the crop. Preferably, the delivery devices will include a means for the predator mites to be released from the composition onto the crop. Such means may be in the form of one or more emergence holes. Preferably, the delivery device is designed or otherwise placed in the crop environment such that the composition inside the device will not get wet upon rainfall or watering of the crop. Depending on the design of the delivery device, it may be suspended from or hung on branches throughout the crop so that the predator mites are released at regular spatial intervals throughout the entire crop.

In one aspect of the invention, the mite composition will be sprinkled as a loose product onto the crop from bottles. In another aspect of the invention, the mite composition will be placed in the crop in sachets or release boxes. In a further aspect of the invention, the mite composition will be blown into the crop using handheld or motor-driven blowers, tractor-mounted delivery systems, systems which drop dry product onto a spinning disc, or systems that sprinkle product from bottles or flasks attached to a rotating arm.

In one aspect of the invention, the composition further comprises a food source for *Thyreophagus entomophagus*. In one embodiment, the food source is a natural diet for *Thyreophagus entomophagus*. Since *Thyreophagus entomophagus* is a grain mite, the food source may be derived from grain. In one embodiment, the food source comprises bran, rice hulls, rolled oats, corn grits, flour (such as gram flour, buckwheat flour or cereal flours), dried fruit, jam, dried insects or poultry meal. In another embodiment, the food source is an artificial diet. A carrier material such as buckwheat husks may also be present.

In a further aspect of the invention, the food source for *Thyreophagus entomophagus* is sugar-rich. The term "sugar-rich diet" in this context is defined as one that contains at least 5% sugar. A sugar-rich diet is useful for rearing prey mites that are more palatable for predator mites. Predator mites favour prey mites fed on sugar-rich diets compared to those reared on low-sugar diets. Therefore prey mites reared on sugar-rich diets provide a better food source for predator mites. As a result, predator mites are healthier and less stressed, leading to increased egg production and the production of a greater number of predators.

Matsumoto, K (Jap. J. Sanit. Zool. 15, 17-24; Jap. J. Sanit. Zool. 16, 86-89; and Jap. J. Sanit. Zool. 16, 118-122) discloses that *Carpoglyphus lactis* uses glucose and sucrose, but not starch, and that its maximum rate of increase is achieved when reared on a diet of 60% yeast and 40% sugar. Matsumoto also discloses that *Tyrophagus putrescentiae* can metabolise a variety of carbohydrates, but that it reaches its maximum rate of increase on pure dried yeast. Further, it describes that in mixed populations, *C. lactis* predominates in diets containing up to 40% sugar, and *T. putrescentiae* predominates in pure dried yeast.

In a further aspect of the invention, the food source for *Thyreophagus entomophagus* is low in starch content. A low starch content is less than 30% starch. In a further aspect of the invention, the predatory mite is *Amblyseius swirskii*. A sugar-rich and/or low-starch food source may be used in conjunction with the present invention in any of the methods for rearing predatory mites, or compositions described above.

In one embodiment, the food source is a yeast-based artificial diet. In another embodiment, the food source contains simple sugars. Simple sugars include those such as allose, altose, dextrose, glucose, sucrose, mannose, gulose, idose, galactose, talose, fructose, saccharose, lactose and arabinose. Preferably, the simple sugar in the diet is dextrose. For example, the diet may comprise 5%, 10%, 15%, 20%, 25%, 30%, 40%, 50%, 60% or more than 60% simple sugars. In a further embodiment, the food source has a low starch content, for example less than 30%, suitably less than 20%, more suitably less than 10%, more suitably still less than 5%, most suitably less than 1% starch. In one embodiment, there is more sugar in the diet than starch. In a further embodiment, the ratio of simple sugars to starch in the diet ranges from 1:1 to 1000:1. Suitably the ratio of simple sugars to starch in the diet ranges from 2:1 to 10:1.

A sugar-rich diet is useful for rearing *Thyreophagus entomophagus* because this mite is able to metabolise simple sugars. Many other mites, such as *Tyrophagus putrescentiae* and *Acarus siro* favour starch-rich diets and lack a direct ability to utilise simple sugars in their diet. In contrast, *Thyreophagus entomophagus* can utilise both simple sugars and starch (Akimov et al. Ekologiya (Ekaterinburg, Russian Federation) 2, 27-31). Diets that are rich in starch rapidly become infested with *T. putrescentiae*, which rapidly overwhelms other mites such as *Thyreophagus entomophagus*. Therefore, a diet low in starch and rich in simple sugars is useful to reduce or even prevent the onset of contamination by other mite species. *T. putrescentiae* does not thrive on low starch diets because it needs to search for food, and the starch food runs out quickly.

Optionally, the diet may additionally contain other food sources that are desirable for the predator and/or prey mites to feed on. For example, the diet may contain pollen such as that from *Typha* sp., date palm plant *Phoenix dactylifera*, or castor oil plant *Ricinus communis*.

Non-limiting examples of possible diet recipes that can be used in accordance with the present invention include: i) 60% yeast, 20% wheat germ and 20% fish food; ii) 50% yeast and 50% dextrose; iii) 55% yeast, 25% dextrose, 10% wheat germ and 10% fish food; and iv) 30% yeast, 30% dextrose, 20% wheat germ, and 20% soya flour. The present invention includes obvious variants of these diets that would be readily contemplated by the person skilled in the art.

According to the present invention, there is provided a method for controlling pests in a crop comprising providing a predator mite that has been reared using *Thyreophagus entomophagus* as a host. In one embodiment, the predator mite is *Amblyseius swirskii*, and the pests are thrips and/or whitefly. *Amblyseius swirskii* is a preferred predator mite since it feeds on either thrips or whitefly. Both thrips and whitefly are major pests of crops, especially in closed cropping environments such as glasshouses. Using *Amblyseius swirskii*, both of these crop pests can be controlled using a single biological control product. The present invention is used for controlling any crop pests, such as one or more listed above. Further the present invention is used in conjunction with any crop, such as one or more of those listed above. Suitably, the crop is selected from the group consisting of peppers, cucumbers, aubergines, roses, gerberas, melons and beans.

According to the present invention, there is provided the use of *Thyreophagus entomophagus* as a rearing host for predatory mites. In one aspect of the invention, *Thyreophagus entomophagus* is used as a rearing host for *Amblyseius swirskii*.

According to the present invention, there is provided a method of rearing mites comprising providing a sugar-rich food source, and allowing the mites to feed on said food source. In one aspect of the invention, the food source is low in starch content. In another aspect of the invention, the food source comprises simple sugars. Simple sugars include those such as allose, allose, dextrose, glucose, sucrose, mannose, gulose, idose, galactose, talose, fructose, saccharose, lactose and arabinose. Suitably, the food source comprises dextrose. This method can be used to rear any mites that are able to metabolise sugars. In a further aspect of the invention, the mites to be reared are *Thyreophagus entomophagus*.

According to the present invention, there is provided a mite food source that is high in sugar and low in starch content. In one aspect of the invention, the mite food source is derived from yeast. Suitably the yeast is brewers yeast, bakers yeast, molasses yeast or lactic yeast. More suitably, the yeast is brewers yeast. The mite food source is particularly suitable for rearing *Thyreophagus entomophagus*, and other prey mites that metabolise sugars such as *Carpoglyphus lactis, Glycyphagus destructor, G. domesticus, G. ornatus, G. geniculatus, Ctenoglyphus plumiger* and *Suidasia medanensis*. In particular, the mite food source is suitable for rearing *Thyreophagus entomophagus* and/or *Carpoglyphus lactis*. The mite food source is also used for rearing prey mites to support a breeding population of predator mites, such as *Amblyseius swirskii*.

EXAMPLES

Example 1

Comparative Productivity of *Amblyseius swirskii* when Reared on Two Species of Prey Mite, *Carpoglyphus lactis* or *Thyreophagus entomophagus*

1.1 Background

A series of cultures of *Amblyseius* (*Typhlodromips*) *swirskii* were setup on two different prey mites, *Thyreophagus entomophagus* and *Carpoglyphus lactis*. The food source for the prey mites was a 50:50 mixture of brewers yeast and dextrose for all cultures except cultures 3 and 8 using *Thyreophagus entomophagus* as prey mites. The *Thyreophagus entomophagus* prey mites in cultures 3 and 8 were reared on a diet without dextrose, and incorporating fish meal as a source of protein. In all cases, the food was mixed with a carrier material.

The number of predator mites per liter of culture material in late stage cultures was counted. Counts were made according to a dry counting method previously used as a standard by MAFF (Griffiths et al. 1976, Ann. App. Biol. 82, 180-185). This method allows multiple samples to be assessed within a short period of time, although it is recognised that it does not recover all of the mites in a sample.

In total, there were 34 cultures using *Thyreophagus entomphagus* as prey mite, and 56 cultures using *Carpoglyphus lactis*.

1.2 Culture Density

Table 1 below indicates the average density of *A. swirskii* per liter of culture material.

TABLE 1

| Culture | Number of *A. swirskii* per litre of culture material, using: *Thyreophagus* as prey mite | *Carpoglyphus* as prey mite |
|---|---|---|
| 1 | 150,000 | 115,000 |
| 2 | 120,000 | 90,000 |
| 3 | 40,000* | 100,000 |
| 4 | 100,000 | 90,000 |
| 5 | 150,000 | 100,000 |
| 6 | 160,000 | 50,000 |
| 7 | 120,000 | 90,000 |
| 8 | 20,000* | 100,000 |
| 9 | 65,000 | 90,000 |
| 10 | 100,000 | 50,000 |
| 11 | 90,000 | 120,000 |
| 12 | 100,000 | 65,000 |
| 13 | 90,000 | 80,000 |
| 14 | 150,000 | 100,000 |
| 15 | 100,000 | 95,000 |
| 16 | 80,000 | 80,000 |
| 17 | 100,000 | 100,000 |
| 18 | 100,000 | 80,000 |
| 19 | 100,000 | 50,000 |
| 20 | 60,000 | 60,000 |
| 21 | 80,000 | 90,000 |
| 22 | 60,000 | 85,000 |
| 23 | 80,000 | 150,000 |
| 24 | 75,000 | 80,000 |
| 25 | 90,000 | 80,000 |
| 26 | 90,000 | 56,000 |
| 27 | 80,000 | 64,000 |
| 28 | 75,000 | 65,000 |
| 29 | 80,000 | 80,000 |
| 30 | 100,000 | 80,000 |
| 31 | 80,000 | 20,000 |
| 32 | 80,000 | 75,000 |
| 33 | 100,000 | 20,000 |
| 34 | 100,000 | 65,000 |
| 35 | n/a | 75,000 |
| 36 | n/a | 65,000 |
| 37 | n/a | 20,000 |
| 38 | n/a | 75,000 |
| 39 | n/a | 75,000 |
| 40 | n/a | 65,000 |
| 41 | n/a | 65,000 |
| 42 | n/a | 20,000 |
| 43 | n/a | 40,000 |
| 44 | n/a | 60,000 |
| 45 | n/a | 65,000 |
| 46 | n/a | 60,000 |
| 47 | n/a | 20,000 |
| 48 | n/a | 40,000 |
| 49 | n/a | 65,000 |
| 50 | n/a | 60,000 |
| 51 | n/a | 50,000 |
| 52 | n/a | 65,000 |
| 53 | n/a | 130,000 |
| 54 | n/a | 65,000 |
| 55 | n/a | 40,000 |
| 56 | n/a | 20,000 |
| Average (mean) | 93,088 | 70,625 |

*Prey mites reared on diet without dextrose

The results indicate that, on average, 31.81% more predator mites were produced by rearing on *Thyreophagus* than on *Carpoglyphus*. A statistical analysis of the results was made using the "t test", assuming equal variances incorporated in the Data Analysis package in Microsoft Excel. This result was found to be statistically significant, having a P value of 0.006394.

The *Thyreophagus* mites in cultures 3 and 8 were reared on a different diet to all other cultures, namely one that did not contain dextrose. The number of predator mites produced when reared on *Thyreophagus* is not as high when the prey mite is fed on a dextrose-free diet than on a diet containing dextrose. When *Thyreophagus* reared on cultures 3 and 8 are excluded from the analysis of the data in table 1, the mean number of *A. swirskii* mites produced on *Thyreophagus* cultures is 97,031, and on *Carpoglyphus* was 70,625. This indicates that, comparing production on constant diets, on average 37.39% more predator mites were produced by rearing on *Thyreophagus* than on *Carpoglyphus*. This result is statistically significant, having a P value of 0.00001597.

1.3 Population Growth

The culture batches from example 1.1 were tracked throughout the later part of the culture development cycle. At 5 different culture stages, the number of *Amblyseius swirskii* predator mites was counted in each culture by the sampling method described above. The 5 culture stages are defined by the number of weeks after starting the culture. Stage 1 is culture week 8, and has a total culture volume of approximately 2 liters. Stage 2 is culture week 9, and on average has a total culture volume of approximately 6 liters. Stage 3 is culture week 10, and on average has a total culture volume of approximately 15 liters. Stage 4 is culture week 11, and on average has a total culture volume of approximately 45 liters. Stage 5 is culture week 12, and on average has a total culture volume of approximately 135 liters.

It is important to note when interpreting these figures that cultures are started in low volumes of carrier material with relatively small numbers of mites. As the mite population density increases, the culture volume is increased to maintain a relatively constant mite density. These figures are obtained by multiplying the density recorded at each stage by the volume of culture which exists. Counts are not made at earlier stages of the culture (i.e. before culture week 8) because the disturbance involved in the small volumes of culture which exist at those stages would adversely affect mite performance and colony growth. Therefore, even at culture stage 1, the number of predator mites has already been influenced by the type of prey mite available, and the nature of the food supplied to that prey mite.

TABLE 2 this includes all culture batches referred to in Table 1

| Culture stage | Actual yield of *A. swirskii* (thousands of mites): *Thyreophagus* | *Carpoglyphus* |
|---|---|---|
| 1 | 189.00 | 119.27 |
| 2 | 563.33 | 467.40 |
| 3 | 1,218.75 | 1,275.00 |
| 4 | 3,085.71 | 3,318.75 |
| 5 | 11,250.00 | 9,642.86 |

TABLE 3 this includes all culture batches referred to in Table 1 except *Thyreophagus* culture batches 3 and 8, having no sugars in diet

| Culture stage | Actual yield of *A. swirskii* (thousands of mites) | |
|---|---|---|
| | *Thyreophagus* | *Carpoglyphus* |
| 1 | 188.75 | 119.27 |
| 2 | 552.86 | 467.40 |
| 3 | 1,475.00 | 1,275.00 |
| 4 | 4,320.00 | 3,318.75 |
| 5 | 16,875.00 | 9,642.86 |

The data shows that cultures of *Amblyseius swirskii* reach significantly higher average densities when fed on *Thyreophagus entomophagus* than when fed on *Carpoglyphus lactis*. Moreover, cultures reared on *T. entomophagus* with dietary sugar perform better than those reared on *T. entomophagus* without dietary sugar. Thus both the species of prey mite offered, and the diet on which that prey mite is reared, influence the final density of the cultures achieved.

Example 2

Rearing of *Amblyseius cucumeris* on *Thyreophagus entomophagus*

A small culture of *Thyreophagus entomophagus* was found to be contaminated with large numbers of the predatory mite *Amblyseius* (*Neoseiulus*) *cucumeris*. The source of this contamination was unknown. Due to the large numbers of *A. cucumeris* visible, the culture was counted. Four thousand *A. cucumeris* were present in the culture, which had a volume of 24 cm$^3$. This is equivalent to a density of 167,000 mites per liter, which exceeds typical production densities of 110,000 mites/liter for *A. cucumeris* fed on *Tyrophagus putrescentiae*.

The culture was kept and expanded. Initially, the culture was transferred to a 265 cm$^3$ flask, with the addition of 40 cm$^3$ of *T. entomophagus* culture, 80 cm$^3$ of fresh bran, and 10 cm$^3$ of food for the prey mites (a 50:50 mix of brewers yeast and dextrose), giving an approximate total volume of 154 cm$^3$ of culture medium. 5 days later the culture flask was examined, and seen to contain very high mite densities. It was then transferred to a 650 cm$^3$ flask, with the addition of an additional 20 cm$^3$ of fresh bran. Nine days later, the culture was counted and found to contain 40,000 *Amblyseius cucumeris*. Thus, the total population increased 10 fold within 14 days, and the density of *A. cucumeris* rose to 230,000 per liter. This is more than double the density which is routinely achieved for *A. cucumeris* during more than 18 years of commercial production of this predator on a diet of *Tyrophagus putrescentiae*.

Example 3

Testing the Effects of the Species of Prey Mite Offered, and the Food Given to that Prey Mite, on the Productivity of the Predatory Mite *Amblyseius* (*Typhlodromips*) *swirskii*

3.1 Background

A trial was set up to assess the influence of prey mite species and prey mite food type, on the production of the predatory mite *Amblyseius* (*Typhlodromips*) swirskii. Three food mixtures were used for this trial, as shown in table 4.

TABLE 4

| | Dextrose | Yeast | Wheat germ | Fish food |
|---|---|---|---|---|
| Diet A | 50% | 50% | | |
| Diet B | | 60% | 20% | 20% |
| Diet C | 25% | 55% | 10% | 10% |

A 50:50 mix by volume of each of the individual food blends with bran was placed into Eppendorf® tubes with the lids removed. The individual tubes were each loaded with 10 reproductive prey mite females and one male, then plugged with cotton wool and placed upright in racks.

Tubes containing the mite *Carpoglyphus lactis* were placed at an ambient relative humidity of 75% and a temperature of 24° C. Higher humidity resulted in a complete deliquescence of the food in previous trials with *C. lactis*. Tubes containing *Thyreophagus entomophagus* were placed into closed polypropylene boxes, and a relative humidity of 80% maintained by a solution of glycerol in water.

Mite populations were allowed to develop for four weeks, and fed fresh food after 2 weeks to maintain population growth. At the end of four weeks, an individual female of *Amblyseius* (*Typhlodromips*) *swirskii* was placed into each tube, and the tube re-plugged with cotton wool. After a further seven days, tubes were opened and the numbers of *A. swirskii* eggs, juveniles and adults counted. For *Thyreophagus entomophagus* tests, five replicates were performed, and for *Carpoglyphus lactis,* 10 replicates were performed.

3.2 Results

The average (mean of all replicates) numbers of eggs, juveniles and adults is given in Table 5.

TABLE 5

Mean results (average numbers of eggs, juveniles and adults)

| | *Thyreophagus entomophagus* | | | | *Carpoglyphus lactis* | | | |
|---|---|---|---|---|---|---|---|---|
| | Eggs | Juveniles | Adults | Total | Eggs | Juveniles | Adults | Total |
| Diet A | 1 | 3.6 | 3.2 | 7.8 | 0.3 | 2.7 | 0.6 | 3.6 |
| Diet B | 0.4 | 0.2 | 1 | 1.6 | — | — | — | — |
| Diet C | 0.8 | 2.8 | 3.2 | 6.8 | 1.3 | 1.9 | 1 | 4.2 |

Both diets containing dextrose (A and C) produced substantial increases in the numbers of predatory mites over the course of the trial. On diet A, *Thyreophagus entomophagus* produced more than double the number of *A. swirskii* than did *Carpoglyphus lactis* fed on the same diet. On diet C, *Thyreophagus entomophagus* produced 38% more *A. swirskii* than did *Carpoglyphus lactis* fed on the same diet. The presence of additional sources of protein in diet B resulted in poor mite reproduction, and in the case of *Carpoglyphus lactis*, the mites performed so poorly on this diet that no *A. swirskii* were introduced.

The results were statistically analysed using Students t test (from the statistical analysis tools included with Microsoft Excel), as shown in tables 6 and 7.

TABLE 6

Comparison of different food blends

| | Diet A vs Diet B | Diet A vs Diet C | Diet B vs Diet C |
|---|---|---|---|
| *T. entomophagus* | 0.002607** | 0.243641 | 0.000265*** |
| *C. lactis* | n/a | 0.342261 | n/a |

TABLE 7

Comparison of different prey mite species

| | *T. entomophagus* v *C. lactis* |
|---|---|
| Diet A | 0.01374* |
| Diet B | n/a |
| Diet C | 0.022953* |

n/a = comparison not possible due to lack of data
*Significant difference
** Highly significant difference
*** Very highly significant difference The results clearly show that the presence of dextrose in the diet gives very significant improvements in productivity of *A. swirskii* fed on either prey mite species. Further, when given the same diet, *Thyreophagus entomophagus* is superior to *Carpoglyphus lactis* as a prey mite for rearing *Amblyseius swirskii.*

The invention claimed is:

1. A method for rearing predatory mites,
- providing a food source for prey mites that comprises dextrose;
- rearing *Thyreophagus entomophagus* prey mites on said food source;
- providing predatory mites that feed on *Thyreophagus entomophagus* in a starting ratio of predatory mites to prey mites from 1:10 to 1:100, and
- rearing the predatory mites on said prey mites, to create a breeding population.

2. The method according to claim 1, wherein the prey mites are present as a breeding population.

3. The method according to claim 2, wherein the predatory mites are from the family Phytoseiidae.

4. The method according to claim 3, wherein the predatory mites are from a genus selected from the group consisting of *Amblyseius, Typhlodromips, Neoseiulus, Typhlodromalus, Euseius, Typhlodromus, Iphiseius* and *Kampimodromus.*

5. The method according to claim 4, wherein the predatory mites are selected from the group consisting of *Amblyseius andersoni, Amblyseius californicus, Amblyseius cucumeris, Amblyseius fallacis, Amblyseius limonicus, Amblyseius montdorensis, Amblyseius ovalis, Amblyseius stipulatus, Amblyseius swirskii* and *Amblyseius womersleyi.*

6. The method according to claim 5, wherein the predatory mites are *Amblyseius swirskii.*

7. A method for controlling pests in a crop comprising releasing into the crop, or the crop growing locus, a predator mite that has been reared according to claim 1.

8. The method according to claim 7, wherein the predator mite is *Amblyseius swirskii*, and the pests are thrips and/or whitefly.

9. The method according to claim 8, wherein the crop is selected from the group consisting of peppers, cucumbers, aubergines, roses, gerberas, melons and beans.

10. A composition comprising at least one predatory mite, and *Thyreophagus entomophagus* in a starting ratio of predator to prey mites from 1:10 to 1:100, wherein the sedentary nature of *Thyreophagus entomophagus* makes it suitable as a food source for said predatory mite.

11. The composition according to claim 10, further comprising a food source for *Thyreophagus entomophagus.*

12. The composition according to claim 11, wherein the food source for *Thyreophagus entomophagus* contains at least 5% sugar.

13. The composition according to claim 12, wherein the food source for *Thyreophagus entomophagus* contains less than 30% starch.

14. The composition according to claim 10, wherein the predatory mite is *Amblyseius swirskii.*

* * * * *